United States Patent [19]

McCue

[11] 4,304,672
[45] Dec. 8, 1981

[54] STORED BLOOD AND LIQUID SYSTEM PH CONTROL METHOD AND APPARATUS

[75] Inventor: John P. McCue, San Diego, Calif.

[73] Assignee: SBR Lab, Inc., Elgin, Ill.

[21] Appl. No.: 892,371

[22] Filed: Apr. 4, 1978

[51] Int. Cl.³ .................... B01D 31/00; B01D 13/00; A61M 31/00

[52] U.S. Cl. .................. 210/638; 210/634; 210/927; 424/19; 424/157; 210/321.1; 210/645; 435/2

[58] Field of Search .......... 210/38 R, DIG. 23, 22 R, 210/22 A, 22 D, 321 R, 321 A, 321 B; 195/1.8; 435/3.4; 422/239; 252/408, 312; 424/219, 148, 157, 158, 163, 93; 260/112 B, 113

[56] References Cited

U.S. PATENT DOCUMENTS

| | | | |
|---|---|---|---|
| 2,276,986 | 3/1942 | Kemp et al. | 210/22 X |
| 2,734,015 | 2/1956 | Wettstein et al. | 210/22 X |
| 3,524,913 | 8/1970 | Snyder et al. | 424/157 |
| 3,573,006 | 3/1971 | Shih et al. | 424/157 X |
| 3,669,880 | 6/1972 | Marantz et al. | 210/38 R X |
| 3,743,480 | 7/1973 | Falk | 195/1.8 X |
| 3,842,000 | 10/1974 | Pawson | 210/38 R X |
| 3,953,329 | 4/1976 | Updike | 210/22 R |
| 4,025,308 | 5/1977 | Holman et al. | 23/230 R |
| 4,077,407 | 3/1978 | Theeuwes et al. | 424/19 X |
| 4,082,509 | 4/1978 | Talcott | 195/1.8 X |

FOREIGN PATENT DOCUMENTS 452000 8/1936 United Kingdom .................. 210/22

Primary Examiner—Frank A. Spear, Jr.
Attorney, Agent, or Firm—Dulin, Thienpont & Potthast, Ltd.

[57] ABSTRACT

Method and apparatus for continuous pH control of aqueous liquid systems, particularly biological and biochemical systems such as stored blood, by sorption of $H^+$ and/or $OH^-$ ions with a passive ion acceptor material isolated from, but in contact with liquid of said system in a selectively permeable membrane packet. Liquid systems of interest are those with an initial pH in the range of from about 4.5 to 9.0, and the pH of the system is maintained by the invention at its initial value, or brought within, and maintained in, the range of from about 6.5 to 8.0. The ion acceptor material is selected from an inorganic, relatively water insoluble metal oxide, hydroxide, phosphate or silicate matrix, which matrix is capable of maintaining a quasi-equilibrium pH state with the aqueous liquid system. The matrixing metals are preferably selected from Ti, Al and B. The matrices may be doped with oxides or hydroxides of Mg, Ca, Zn, Fe, Cu, Co, Cr and V to permit predetermined selection of a desired quasi-equilibrium pH value, and to adjust effective base capacity. Cation (e.g., $Na^+$ and $K^+$) doping may be used to expand the matrix lattice structure and help maintain electric (ionic) neutrality. Typical matrix acceptor compounds are selected from $Al_2O_3$, anhydrous $Al(OH)_3$, $Al(OH)_3$ gel (preferred), $MgHPO_4$, and $Mg_2Si_3O_8$.

49 Claims, 14 Drawing Figures

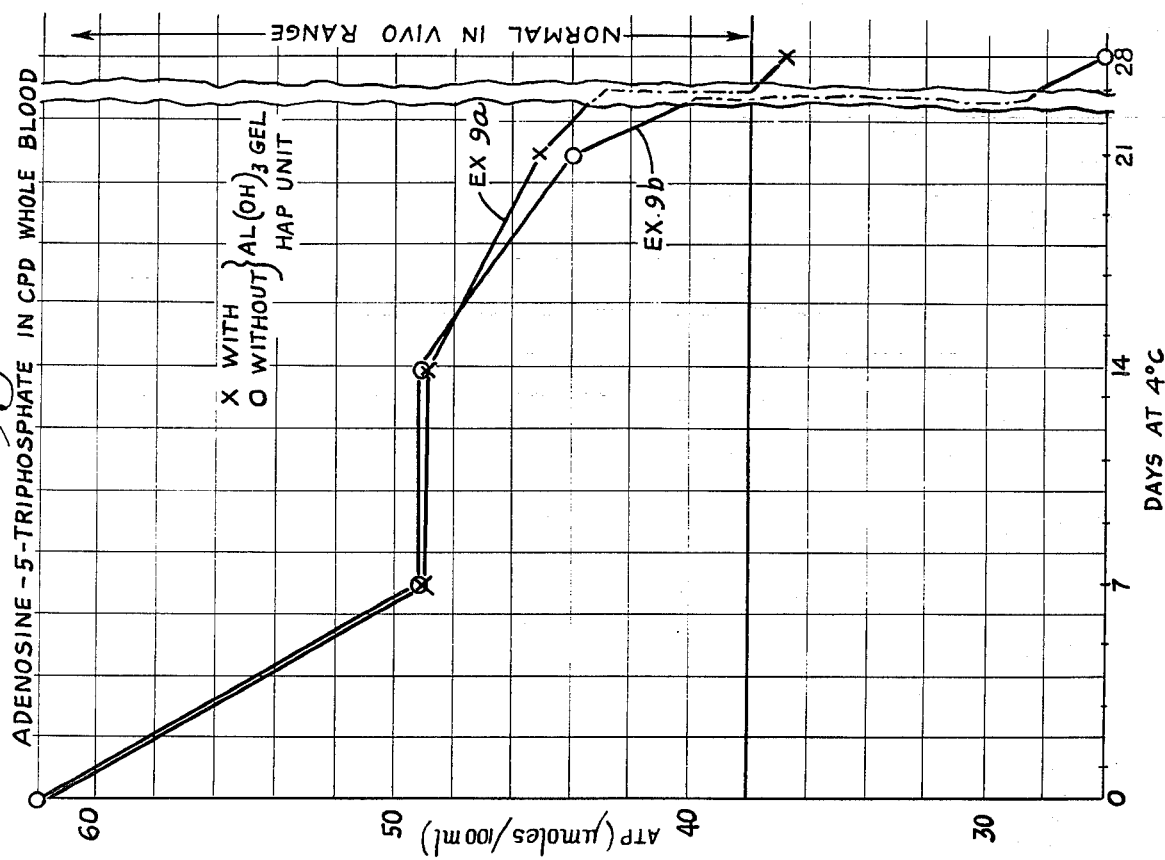
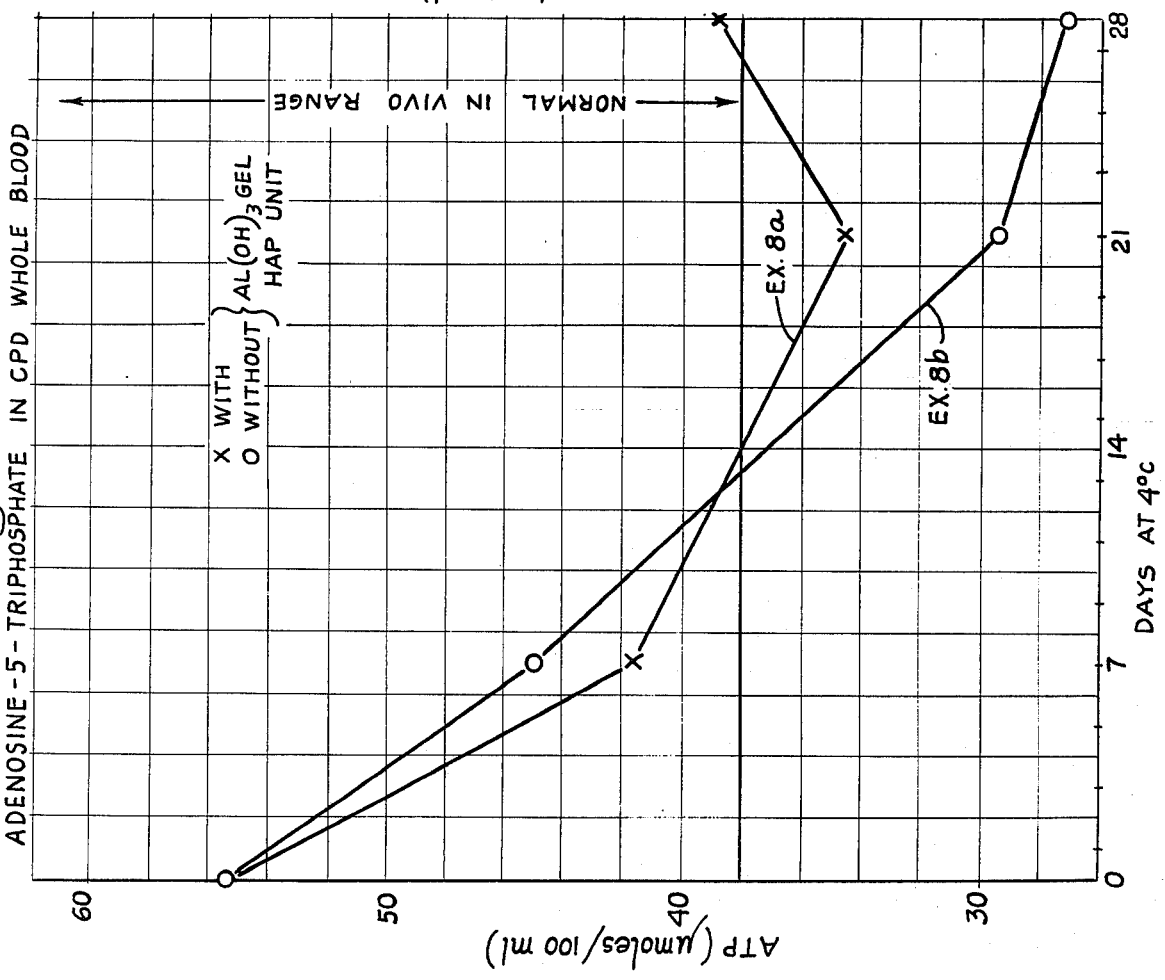

STORED BLOOD AND LIQUID SYSTEM PH CONTROL METHOD AND APPARATUS

FIELD

This invention relates to continuous control of pH in aqueous liquid systems by methods and means of passive sorption of $H^+$ or $OH^-$ ions occurring in such systems by means of an inorganic, relatively water insoluble oxide, hydroxide, phosphate or silicate matrices selected from Al, Ti, and B that are in quasi-equilibrium with the aqueous systems of interest. The matrix acceptor material may be doped with a variety of compounds. These ion acceptor matrices are isolated from the liquid system in a membrane packet that selectively passes hydrogen and/or hydroxide ion and other selected ions thereinto at a predetermined rate to control the $H^+$ and/or $OH^-$ ion acceptance kinetics. The invention more particularly relates to control of pH by withdrawing $H^+$ or $OH^-$ ions by such hydrogen acceptor material at a rate at which the ions occur in the system external to the packet of hydrogen acceptor material. Specific embodiments in biologic and biochemical systems are illustrated by way of example, chief among them being stored blood preservation and pH control.

BACKGROUND

The maintenance of pH in liquid systems is extremely important to the operation and integrity of such systems, particularly where there is continuous generation of hydrogen ions due to activity in such systems. This activity may manifest itself in the form of chemical reactions, in the form addition of hydrogen ion to the systems from an external source, or from the environmental context of such systems, for example the introduction into such systems of hydrogen ions by dissolution or leaching. Many inorganic reactions produce hydrogen ions as a by-product, or are pH sensitive. In the area of pollution control, for example, many waste effluents are particularly characterized by having a low pH which must be neutralized without the addition of other soluble cations such as sodium which in turn are pollutants. Thus, neutralization of acidic pickling liquors by use of sodium hydroxide results in a waste stream containing substantial quantities of sodium sulfate which cannot be disposed of because of the high dissolved sodium sulfate solids content.

Similarly, biochemical reactions and functions of biological systems are pH dependent. There is a particular pH for every enzyme at which its activity is optimal; there are specific pH ranges in which an organism will grow and others in which it may synthesize certain molecules; and there are specific pH ranges in which a cell must be kept in order for it to maintain itself.

At present, control of pH in biological reactions in vitro is achieved with the use of chemical buffers having pK values in the range 6.5 to 8.0. Of the limited number of such buffer systems available, only the phosphates and carbonates are non-toxic. However, even these two buffers present problems for pH maintenance of cellular systems. For example, at the concentration of phosphate required to maintain pH in the system of stored red blood cells, the cells undergo tremendous osmotic stress due to the redistribution of water across the cell membrane in response to the difference in phosphate ion concentration inside and outside the cells. Further, the buffering capacity of the phosphate is lost at the temperatures required for storage (preservation) of these cells. As for the carbonate systems, their pK values allow them to buffer only at the extremes of the physiological range (i.e., pH 6.5 and 8.0). Recently, Harmening and Dawson (The Use of Ion Exchange Resins as a Blood Preservative System, 30th Annual Meeting of the American Association of Blood Banks, Atlanta 1977) have proposed use of ion exchange resins to control pH in some biological systems in vitro. However, such materials tend to decompose on standing, permit toxic monomers or plasticisers to leach out, or may bind essential metal ions, all of which become significant problems for the maintenance of biological systems.

The term fermentation refers to the controlled synthesis of biologicals (e.g., antibiotics, vitamins, steroids) by micro-organisms in aerobic as well as anaerobic processes. The present methods used in industrial fermentation for pH control are:

(1) constant monitoring of pH by glass electrode and titration with required acid or base to regain desired pH;

(2) use of various buffers such as phosphates, carbonates, Tris, etc.

Nearly all fermentation reactions are carried out in the pH range 5 to 10. Production of low molecular weight molecules by micro-organisms is usually carried out in the pH range 5 to 7, such molecules being acetone, butanol and ethanol. Larger molecules such as antibiotics and steriods are produced by micro-organisms in culture at pH 7.0 to 7.5. A general discussion of industrial fermentation processes and pH requirements may be found in *Biochemical and Biological Engineering Science*, Vol. 1, N. Blakebrough, editor, Academic Press, London (1967).

Penicillin fermentation is an example where maintenance of pH in the range 7.0 to 7.4 is required in order to get the micro-organisms (i.e., penicillium notatum and penicillium chrysogenum) to produce the antibiotic. Caden has reported that even though growth of the penicillin molds is facilitated in the pH range 4.5 to 5.0 the production of penicillin by these micro-organisms required the media pH to be in the range of 7.0 to 7.5 (E. L. Caden, J. Biochem. Microbiol. Tech. Engng. 1, 413 (1959). Brown and Peterson have reported that the optimum pH for production of penicillin for prolonged period is 7.0 (W. E. Brown and W. H. Peterson, Industr. Engng. Chem. 42, 1769 (1950). Pirt and Callow recommend a pH below 7.0 for growth of the penicillin mold (Stage I), and a pH between 7.0 and 7.4 for production of penicillin by the mold (Stage II) (S. J. Pirt and D. S. Callow, Nature 184, 307 (1959).

The term "cells in culture" refers to any cells (single or connective) or collection of cells (e.g., organs) that are maintained to some degree in vitro in an aqueous media. The pH range required for storage and growth media used with in vitro maintenance of mamalian cells and organs is 7.0 to 7.4.

Although various "buffers" such as Tris, phosphate, N-tris (hydroxymethyl) methyl-2-aminoethanesulfonic acid, and N-2-hydroxyethylpiperazine-N'-2-ethanesulfonic acid, have been proposed for pH control of tissue culture systems they have not proved adequate for maintenance of normal cell activity. In part this problem arises from the need for bicarbonate in the media. The maintenance of a stable pH in the presence of the easily disturbed bicarbonate-$CO_2$ equilibrium can frequently be a problem, the solution for which has been the use of relatively high levels of phosphate buffers (e.g., greater than 50 mM) or elaborate $CO_2$—$HCO_3^-$ regulating equipment. A general discussion of environmental factors influencing cells in culture can be found in *Growth, Nutrition and Metabolism of Cells in Culture,* Vols. I and II, G. H. Rothblat and V. J. Cristofalo, editors, Academic Press, New York (1972).

There is also a great need to improve the viability of stored blood under more closely physiological conditions so that it is useful over longer periods of time. In 1977 ten to twelve million units of blood will have been collected in the U.S. At present, FDA regulations permit each of these units to be stored three weeks before they can no longer be considered for use for transfusion. This limit in permitted storage time contributes to a loss of collected blood ranging in degree from 20 to 50%. The cost of this loss, at $50.00 a unit, runs over one hundred million dollars a year.

In addition to the inventory, supply, and cost problems resulting from loss due to outdating, there is also the clinical problem of significant biochemical deterioration of the stored bank blood. After two weeks the stored blood has undergone significant biochemical deterioration which can result in a 30% loss in red cell survival after transfusion. The recipient patient also has the burden of "repair" of the deteriorated red cells received, this repair can take from 12 to 72 hours before the transfused blood is returned to a normal state. Such burden of repair may present serious problems to patients receiving large volumes of blood which put added medical strain on the patient. Those red cells that cannot be "repaired" represent an excretory problem and burden.

Thus, there is a great need not only for prolonging the storage life of blood in order to reduce loss due to outdating, but also to improve the quality and viability of blood stored longer than two weeks. Central to achieving the goals of longer shelf life and improved quality of bank blood is the need to continuously control the pH in blood in the narrow pH range of 7.0 to 7.2 while it is being stored in 4° C. In addition to pH, the parameters considered most important to red cell quality are glucose utilization, cell morphology, cellular levels of ATP (adenosine triphosphate) and 2,3-DPG (2,3-diphosphoglycerate). Thus, an improved method of blood storage should maintain a more physiologically compatible pH level, with attendant improved results in maintaining better ATP and 2,3-DPG levels than standard CPD blood at 3 and 4 weeks of storage, and better morphology.

Accordingly, the importance of being able to maintain pH in the range 6.9 to 7.5 is far reaching in medicine, the pharmaceutical industry and the research laboratory. Equally important however is the ability to maintain the pH in an non-interfering, nontoxic and continuous fashion. There is thus a great need for an improved method and apparatus for continuous control of pH in liquid systems, and more particularly in biological and biochemical systems. Important among these latter, there is a great need for improvement in the viability of stored blood during the presently accepted storage term of 21 days, and thereafter, and for improved anticoagulant solutions.

THE INVENTION

OBJECTS

It is among the objects of this invention to provide improved methods and apparatus for the continuous control of pH in liquid systems.

It is another object of this invention to provide for pH control of aqueous liquid systems by means of a passive hydrogen ion acceptor maintained in indirect contact with the liquid system having a content of $H^+$ and/or $OH^-$ ions.

It is another object of this invention to provide continuous control of the pH in liquid systems by withdrawing the $H^+$ or $OH^-$ ion selectively at a rate adjusted to the rate at which the ions occur in that liquid system.

It is another object of this invention to provide a hydrogen ion acceptor packet comprising a selectively permeable membrane within which is dispersed an inorganic, relatively water insoluble passive hydrogen ion acceptor material, which packet may be placed in a variety of liquid systems requiring continuous pH control.

It is another object of this invention to provide a slurry or gel of aluminum oxide, aluminum hydroxide, magnesium hydrogen phosphate, magnesium trisilicate, and mixtures thereof with magnesium hydroxide, zinc oxide, zinc hydroxide, ferric oxide, ferric hydroxide and mixtures thereof dispersed in a special salt solution which acts in combination with a selectively permeable membrane as a passive hydrogen or hydroxyl ion acceptor.

It is another object of this invention to provide a passive ion acceptor material suitable for use in aqueous liquid systems by isolating the acceptor material from the liquid of said system by means of a selectively permeable dialysis membrane.

It is another object of this invention to provide an $H^+$ and/or $OH^-$ ion acceptor matrixing material selected from oxides, hydroxides, phosphates or silicates of Ti, Al, and B.

It is another object of this invention to dope the acceptor matrix materials with compounds of Mg, Ca, Zn, Fe, Cu, Co, Cr and V to permit predetermined selection of a desired quasi-equilibrium pH value, and to adjust effective base capacity.

It is another object of this invention to provide matrix acceptor compounds which can be cation doped to expand the matrix lattice structure and help maintain electric (ionic) neutrality of the liquid system of interest.

It is another object of this invention to provide a hydrogen ion acceptor packet comprising an acceptor material of aluminum hydroxide gel, or a slurry of aluminum oxide, or hydroxide, alone or in combination with magnesium hydroxide, dispersed in a saline solution, optionally with added salt and $MgCl_2$, and which material is disposed in an appropriate dialysis type membrane package.

It is another object of this invention to provide for continuous pH control of inorganic liquid systems, organic liquid systems, biochemical liquid systems, and biological liquid systems.

It is another object of this invention to provide for maintenance of the pH of stored blood by means of the aforesaid hydrogen ion acceptor packet systems.

It is another object of this invention to provide method and means for storage of human blood which show improved pH control during the storage period, as well as improved glycolytic activity, improved ATP levels, improved 2,3-DPG levels, and improved plasma iP levels.

It is another object of this invention to provide a method and means of storage of whole human blood showing improved red cell characteristics during and beyond normal storage periods of 21 days, and provide new anticoagulant solutions.

It is another object of this invention to provide for continuous control of pH levels in fermentation processes, organ storage, enzymatic reactions, in tissue and culture growth in aqueous systems, broths, or on culture media, and pH control for enclosed environmental systems, for example, fish in tanks.

Still other objects will be evident from the detailed disclosure which follows.

FIGURES

The invention is illustrated with respect to the drawings in which:

FIGS. 5a and 5b show typical improved results in the ATP level of stored whole blood using the hydrogen acceptor packets of this invention over a period somewhat greater than 28 days as compared to standard stored whole blood;

SUMMARY

Figure 1:
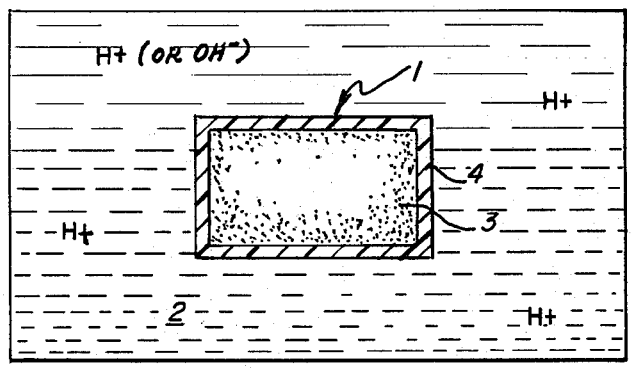
FIG. 1 is a schematic sectional view showing the hydrogen acceptor packet disposed in a liquid system for continuous pH control.

The objects of the invention can be achieved by utilizing the unusual and specific properties of oxides, hydroxides, phosphates and silicates of Al, Ti, and B to form $H^+$ and/or $OH^-$ ion acceptor materials in the form of slurries or gels placed in indirect contact with the liquid system from which the ions are to be removed. The liquid systems of interest are aqueous systems having an initial pH in the range of from about 4.5 to 9.0, and the pH of the liquid system is maintained by the invention at its initial value, or brought within and thereafter maintained in the pH range of from about 6.5 to 8.0. The indirect contact is established by placing the acceptor materials with various salts or salt solutions in hydrophylic dialysis sacks of suitable selectively permeable material, called hydrogen acceptor packets or HAP's in the case of removal of $H^+$ ion. At present, we prefer cellophane or polycarbonate films having selectively permeable pores on the size range of 20 Angstroms. However, any selectively permeable membrane of natural or plastic composition having micropores in the range on the order of from 5 to 25 Angstroms may be employed. When used in a biologic system the membrane is preferred to be of physiologically acceptable non-toxic material.

The passive ion acceptor material is a relatively water insoluble, inorganic metal oxide, hydroxide, phosphate or silicate matrix capable of maintaining a quasi-equilibrium pH state with the aqueous liquid system of interest. The matrixing metal is preferably selected from Al, Ti, and B with Al being the most preferred for the specific biologic/biochemical embodiments discussed herein. The ion acceptor matrix materials may be doped with from about 0.01 to 5 wt. % of oxides or hydroxides of Mg(preferred), Ca, Fe, Cu, Co, Cr and V to permit predetermined selection of a desired quasi-equilibrium pH value, and to adjust (e.g., increase) the effective base capacity. Cation doping (e.g., $Na^+$ and $K^+$ by use of NaCl or KCl solutions) may be used to disrupt or expand the matrix lattice structure, and help maintain electric (ionic) neutrality. Typical acceptor matrix compounds are selected from $Al_2O_3$, anhydrous $Al(OH)_3$, $Al(OH)_3$ gel (preferred), $MgHPO_4$, and $Mg_2Si_3O_8$. Depending on the materials and dopants used, the resulting matrix acceptor systems can act either as a weak base or a weak acid and accept up to one-third their stoichiometric equivalents of ions while maintaining their initial states. Added $MgCl_2$ helps in blood preservation.

While I do not wish to be bound by theory, the following discussion will be helpful in understanding some of the concepts relating to this invention. Although the exact structure of the various matrix species mentioned above are not known, generally accepted structural representations of matrix structures are ones in which the materials are considered to form polymeric lattices. For aluminum hydroxide gel this lattice structure incorporates at least three waters of hydration firmly bound to each ionic aluminum, and the structure can be represented as follows:

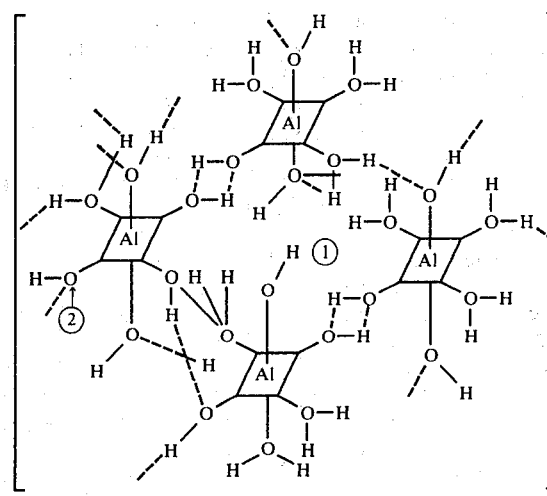

where each oxygen (whether derived from $OH^-$ or $H_2O$ is bound to a lattice aluminum ion and to two $H^+$. In the case of $OH^-$ this results in hydrogen bonding between the $Al(OH)_3 \cdot 3H_2O$ monomers.

This hydrogen bonding produces a lattice structure of significant thermodynamic strength. Further, the relative bond energies for Al—O and H—O are comparable, thus giving rise to the unusual condition of a lattice structure with significant covalent bonding in and between its unit matrices. This results in covalent thermodynamic stability for the entire matrix structure and thus arises the name "polymeric" lattice.

The lattice stability is reflected in an extremely small solubility product constant ($K_{sp}$) of $\sim 5 \times 10^{-33}$. This means that very little free ionic or neutral monomers of aluminum escape the solid matrix (i.e., less than 1 ppm free aluminum). Accordingly, very little free hydroxide ion is released to the surrounding aqueous media. Further, the hydroxide matrix is actually a non-equilibrium system in that thermodynamically it moves toward the formation of an $Al_2O_3$ polymer in which $H^+$ is expelled and covalent Al—O—Al bonds are formed. Kineticly, however, this process is so slow that treatment of aluminum hydroxide gel at elevated temperatures is rquired to complete its conversion to pure aluminum oxide.

These characteristics of the gelatinous aluminum hydroxide matrix results in little tendency to release $OH^-$ to the surrounding media, an ability to adsorb $H^+$ without solubilizing the matrix, and a tendency for the matrix to resist $H^+$ adsorption. These properties result in a quasi-equilibrium state for the aluminum hydroxide matrix being established with distilled water. That means that when gelatinous $Al(OH)_3$ is brought into contact with an aqueous system the two interact to produce a system approximating the properties of distilled water (e.g., pH close to neutrality)

It is this property of aluminum systems to be in quasiequilibrium with pure water, combined with their property of large base reserves in the form of $OH^-$ and $O^=$, that results on the one hand in a strong base character while in contact with strongly acid solutions, and on the other hand results in an extremely weak base character when in contact with solutions near neutrality (i.e., pH 6 to 8).

When anions such as $Cl^-$ are present in the immediately surrounding media, the gelatinous $Al(OH)_3$ matrix is disturbed as these ions enter the matrix. Such anion entry results in a lower lattice stabilization energy and a slight increase in the amount of free $OH^-$ ions released to the surrounding media. When a solubilizing complexing agent such as citrate enters the lattice the lattice is disturbed further with greater release of $OH^-$ but with little effect on release of free $Al^{+3}$ until the amount of complexing agent completely overwhelms the matrix and the solid aluminum phase dissolves. This will not occur until at least one-third of the coordination sites of the aluminum ions in the matrix are occupied by the complexing agent.

The fact that anions such as $Cl^-$ and complexing agents such as citrate or phosphate lower the lattice stabilization energy means that these materials can be added to the suspension of aluminum species or to the surrounding media in order to "open up" the lattice permitting greater adsorption and/or neutralization of $H^+$ ion. Accordingly, "disruption" as used herein refers to the property of anions to open up the matrix lattice structure by ligand substitution or competition for the binding site of $OH^-$ on the matrix metal. In the structure above this occurs where an anion moves into the hydroxyl position identified by the arrow labeled with the number 2.

By "doping" is meant placing small quantities of cations or undissociated normally strong base materials (such as $Mg(OH)_2$, ZnO, $Zn(OH)_2$, $Fe_2O_3$, $Fe(OH)_3$ or the like) into the lattice hole, identified by the number 1 in the structure shown above. While these strong bases do provide for added base equivalents, they do not convert the matrix into a strong base and themselves no longer free to act as strong bases.

The amount of ion acceptor material used depends on the equivalents of the ion in the aqueous liquid system of interest that initial measurement, calculation or experience shows should be accepted (removed) over the period of time required, and is at least from 2 to 4 times such ion equivalents. The quantity of acceptor material (or acceptor system where the material is doped) relates to the amount of ions needed to be removed during the period of interest, while the membrane relates to the rate of withdrawal (acceptance) of the ions. By way of definition, the ion acceptor materials or compounds, when doped and/or dispersed in salt solution, are termed ion acceptor systems, and when disposed in the dialysis sacks are termed ion acceptor pack units. In operation the units may be placed in the aqueous liquid system and left lie therein so that acceptance occurs by diffusion. The units may be suspended in the liquid system, e.g., on a tether such as a plastic filament. The liquid of the liquid system and the unit may be moved relative to each other on a continuous or intermittent basis, as by agitation of the unit, or pumping of the fluid into contact with the unit. The pH of the liquid system can be monitored to assure that the unit is not exhausted, and a fresh unit inserted when the full ion equivalents have been accepted by the initial units(s). The units may be of any convenient size of configuration so long as there is adequate surface area of the dialysis membrane in contact with the liquid of the system to achieve the proper rate of ion acceptance relative to the rate of generation or occurrance in the aqueous liquid system of interest. After preparation, the units may be stored with or without drying (dehydration) to remove excess water, with air drying under refrigeration being presently preferred. The units may be stored and transported in a plastic pouch or glass jar. Drying prior to autoclaving is preferred.

The aluminum oxide and hydroxide acceptor systems in liquid systems having pHs around neutrality function as $H^+$ ion acceptors. In the range above about 8.0, the $Al(OH)_3$ systems can function as $OH^-$ in acceptors. $MgHPO_4$ systems function as $OH^-$ ion acceptors in liquid systems range of pH 7.5-8.0. $Mg_2Si_3O_8$ systems equilibrate at a pH in the range of from 8.0-8.6 wherein they act as $H^+$ ion acceptors.

More specifically, by way of example and not by way of limitation, anhydrous aluminum hydroxide, aluminum hydroxide gel, and solid aluminum oxide are suitable matrixing compounds. These materials may be used alone or mixed with a small percentage of magnesium hydroxide dopant in the range of from 0.01 to 2 wt. %. The order of ability for neutralizing (absorbing or accepting) $H^+$ ion is $Al(OH)_3$ gel > $Al_2O_3$ > anhydrous $Al(OH)_3$.

Such materials employing aluminum in the +3 valence state equilibrate slowly with aqueous media to a final pH close to the physiological range. Thus, these materials, being separated from the liquid media by a suitable selectively permeable membrane, neutralize hydrogen ion at a rate similar to that at which many liquid, inorganic, biochemical or biological (cellular) systems produce it. Thus, a very important aspect of this invention is the ability of the ion acceptor units to effectively "buffer" biologic or biochemical systems by passive ion acceptance in a non-toxic and non-interfering manner, heretofore satisfactorily unattainable by conventional carbonate/bicarbonate/phosphate buffers.

In the case of use of aluminum hydroxide, a gel is formed with a dilute solution of salt, such as a NaCl solution isotonic with respect to the osmolarity of the specific liquid system being treated. In the case of aluminum oxide, or anhydrous aluminum hydroxide, a slurry in the dilute saline solution is formed. This permits maintaining the ionic balance of the unit in the liquid system; as $H^+$ ions migrate inwardly $Na^+$ or $K^+$ ions migrate outwardly, thus maintaining osmotic balance. In addition, the hydrogen acceptor material, aluminum oxide or hydroxide in solid or gel form, may be doped with other materials such as basic oxides or hydroxides to modify the matrix and to adjust the final equilibrium pH of the system and increase the base capacity.

By way of example and not by way of limitation, the present invention has been applied to storage of human red cells under blood banking conditions as a typical biological system to examine and show the usefulness of the aluminum acceptor dialysis membrane system (HAPs) for removal of free hydrogen ion from solutions. These human red cells have a critical dependence on pH, needing to be maintained in the pH range 7.0 to 7.2 during 4° C. storage in order to maintain biochemical integrity and viability. Though only anaerobic in their metabolism, red cells share features common with other mamalian cell types. Among these are the need to be maintained in the same narrow pH range 7.0–7.2 while being handled in vitro. Thus, this work with red cell pH is applicable to other cell systems such as tissue culture and organ banking as well as to liquid blood banking problems.

Further, many micro-organisms used in the pharmaceutical industry need to be maintained, at some point, in a similar pH range. For example, it is necessary to maintain penicillium notatum and chrysogenum in the pH range 7.0 to 7.4 in order to get them to produce penicillin during the industrial fermentation process used to produce this antibiotic. The ion acceptor systems of this invention permit the continuous maintenance of media pH for industrial fermentation processes within the range of 6.9 to 8.0. The particular required pH can be obtained by varying the type and amounts of inorganic salts mixed with the acceptor materials, and the pH can be maintained to within 0.1 units for several weeks (based upon extrapolation from tests with red cells). Most importantly, this pH control is achieved in a passive manner. That is, no chemicals that may influence the metabolism of the micro-organism is added to the fermentation media. This avoids the problem associated with such materials as inorganic phosphates, $NH_3$, carbonate, etc. that are presently used to "buffer" or adjust media pH.

Trace amounts (i.e., less than 1 ppm) of Al(III) released from the dialysis systems do not influence the fermentation processes. In fact, when metal reaction vessels are required for industrial fermentation processes the one of choice is usually aluminum. Further, the passive nature of the aluminum-dialysis system permits pH control without sequestering metabolicly important trace metals from the media. Such sequestering can occur with certain buffer systems (e.g., phosphates) or when strong bases are added (e.g., addition of NaOH can produce metal hydroxide locally that disturb trace metal balance).

With the use of aluminum hydroxide and oxide filled dialysis sacks, pH can be maintained within the necessary range of 7.0 to 7.4 for tissue culture and organ storage work. This permits stabilization of the $CO_2$-bicarbonate equilibrium at an acceptable pH without otherwise influencing cellular activity (e.g., eliminates the osmotic stress and metabolic stimulation of high phosphate levels required with the use of phosphate buffers). Such pH control is required for the systematic study of environmental influences on cells and for maintenance of cells and organs in vitro.

DETAILED DESCRIPTION

The following examples are by way of illustration and not by way of limitation of the principles of the invention.

FIG. 1 shows in schematic cross section a hydrogen acceptor packet 1 within a liquid environment 2 having $H^+$ or $OH^-$ ions that need to be removed. The HAP 1 is comprised of an ion acceptor material 3 within a selectively permeable membrane 4. As a hydrogen acceptor, material 3 may be the slurry form of aluminum oxide, or the gel form of aluminum hydroxide. A portion of either material, from 0.01 to 2% may be magnesium hydroxide, with the balance the aluminum oxide or hydroxide. While the slurry or gel may be in distilled water, the preferred embodiment and best mode is to use the acceptor substance (Al or Al/Mg oxides/hydroxides) in a dilute saline solution, e.g., 0.85 wt % NaCl solution, in the dialysis bag or tube. Under the system conditions the hydrogen ion migrates from the liquid environment 2 (e.g., reaction phase) through the membrane 4 where it reacts as follows:

Eq. 1: $H^+ + (-Al-OH) \rightarrow (-Al-OH_2)^+$ ; or

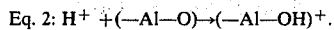

Eq. 2: $H^+ + (-Al-O) \rightarrow (-Al-OH)^+$.

While I do not wish to be bound by theory, the hydrogen ions appear to be accepted into the matrix of the aluminum oxide or hydroxide without destroying its nature as a slurry or polymer.

Figure 2:
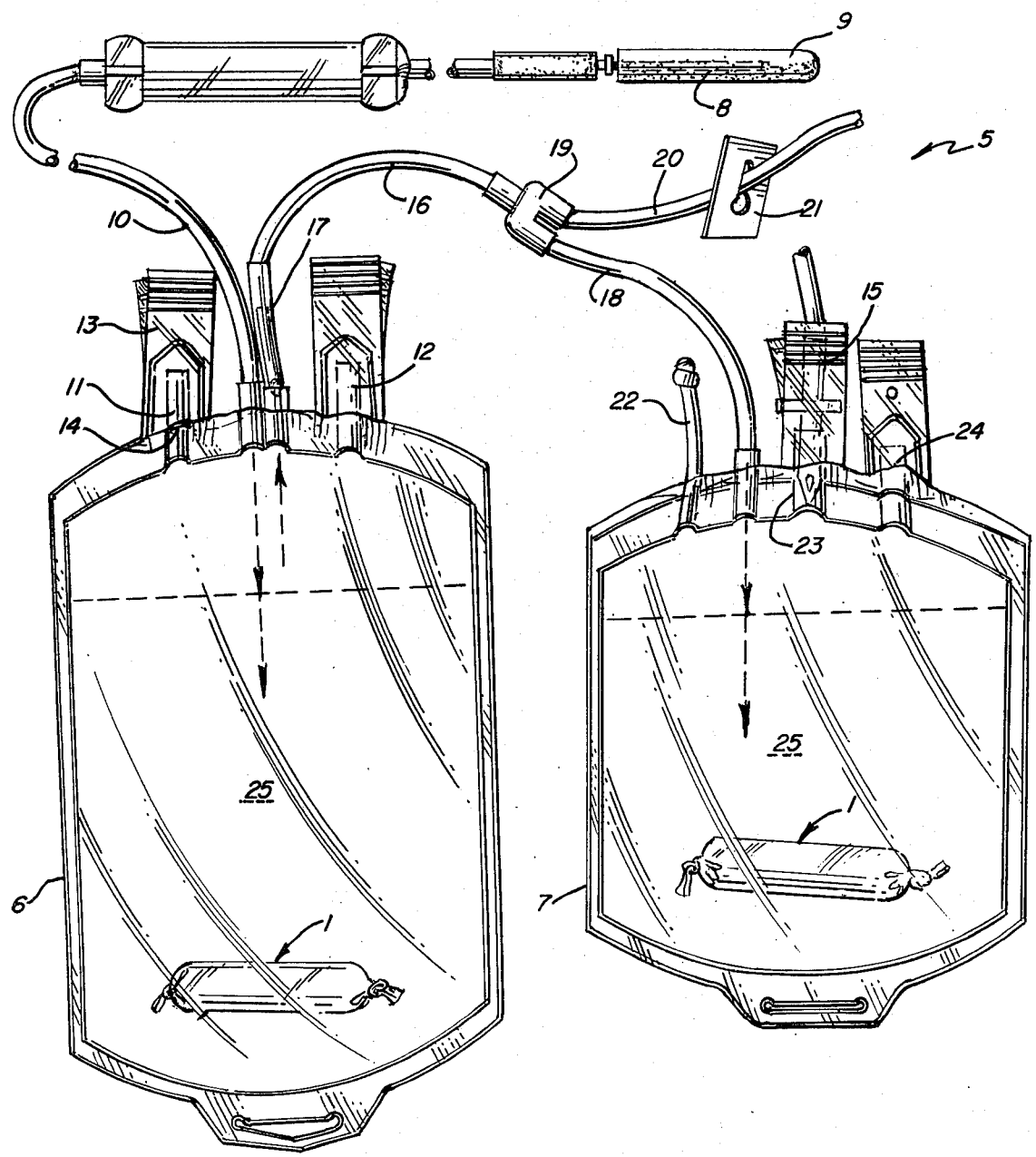
FIG. 2 shows the use of a hydrogen acceptor packet in a blood storage bag.
Figure 3B:
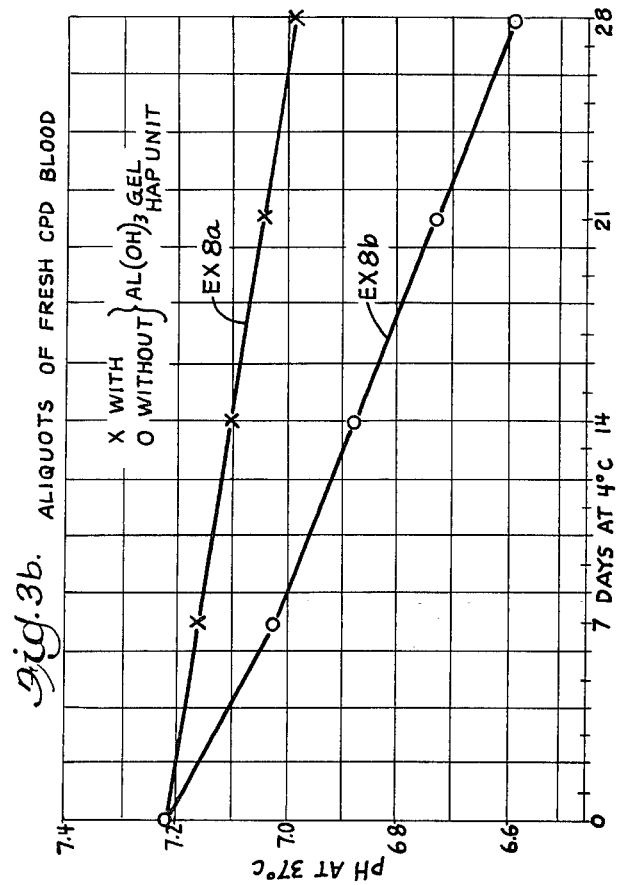
FIGS. 3a–3d are graphs showing typical improvement in control of pH of stored blood over a 28 day period using the hydrogen acceptor system of this invention, as compared to the prior art not using the present invention.
Figure 3D:
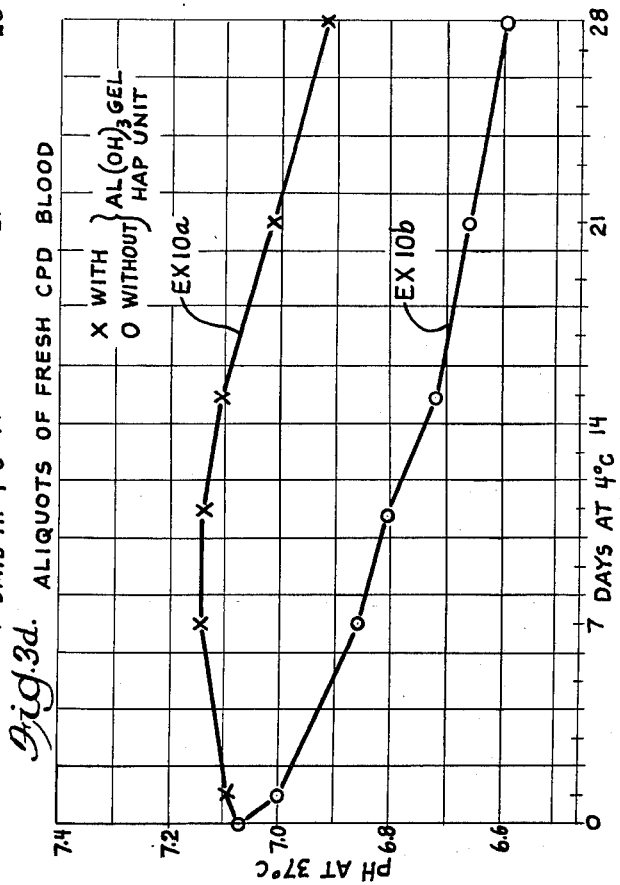
Figure 3A:
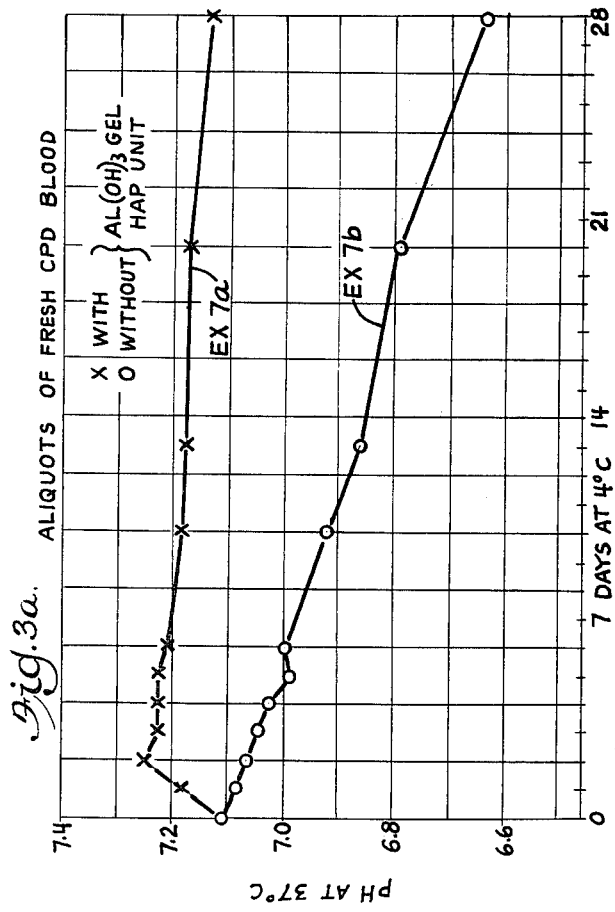
Figure 3C:
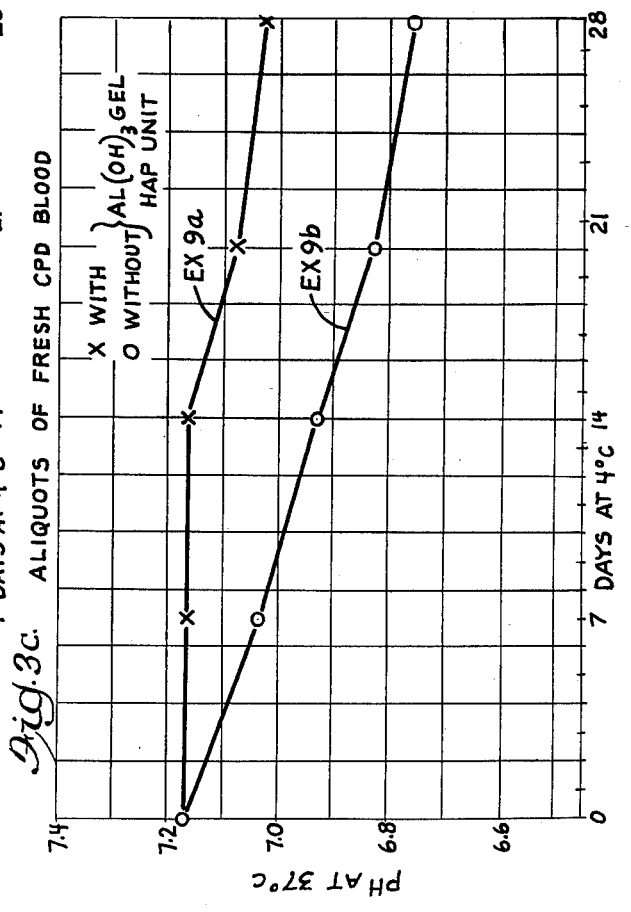

FIG. 2 shows the use of the HAPs (hydrogen acceptor packets) 1 in a blood bag system 5 comprising a storage or transfer bag 6 and an auxiliary or aliquot bag 7. Blood is drawn from a donor (not shown) by means of needle 8 (shown within sheath 9) and delivery tube 10. In the alternative, blood, after first being drawn into a standard blood pack unit (not shown) having anticoagulant CPD or ACD solution therein (such as a Fenwall CPD whole blood (human) "Blood-Pack" unit, containing approximately 450 ml human blood and 63 ml citrate, phosphate, dextrose anticoagulant solution), may be introduced via transfer ports 11 or 12 into the bag 6. The introduction is in the standard manner after opening the sterile seal tab 13 and puncturing the seal rib 14 with a hollow transfer lancet (not shown on bag 6, but shown as 15 on bag 7). An additional or partial aliquot can then be transferred into bag 7 via tube 16 having rib-piercing hollow lancet 17, and tube 18. The Y coupling 19 permits additional aliquot bags (not shown) to be filled via tube 20. Clamp 21 shuts tube 20 when not in use. Samples may be withdrawn from the bags via ports 11, 12, 22, 23, and 24. While FIG. 2 shows a HAP unit 1 in each bag, 6 and 7, it is to be understood that the blood bag 7 need not contain a HAP unit 1 where coagulation is not a drawback. It is preferred that the HAP unit not be immersed in an anticoagulant solution, such as CPD or ACD, for any substantial length of time prior to the introduction of the blood since the anticoagulant and HAP unit will mutually exhaust themselves. Upon blood entering the bag, shown in dashed lines as 25 in bags 6 and 7, the HAP unit commences its action of pH control of the stored blood. The specific examples below demonstrate improved results in ATP, plasma iP, glycolytic activity, and pH control.

PREPARATION OF ACCEPTOR MATERIAL

EXAMPLE 1

General Preparation; Slurry of $Al(OH)_3$.

The various forms of the acceptor material may be prepared simply by suspending the required weight of $H^+$ ion acceptor material (e.g., here solid $Al(OH)_3$) into distilled $H_2O$ and adding 0.03–0.12 g NaCl/5 g $H^+$ ion acceptor material used, mixing and loading the resulting gel or suspension into an appropriate size dialysis tube previously closed at one end. After filling, the tube is closed at the loading end to form a HAP unit. The unit is then washed with distilled water. The unit may be used as is in the $H^+$-containing liquid system, or sterilized in an autoclave in a standard manner prior to use. Sterilization is required for blood storage, organ storage, tissue culture, antibiotic preparation by fermentation, and the like, uses.

EXAMPLE 2

Slurry HAP Unit of $Al_2O_3$.

Example 1, is repeated, using however, porous solid or powdered aluminum oxide in place of the aluminum hydroxide.

EXAMPLE 3a

HAP Unit of $Al(OH)_3$ Gel

Example 1 is repeated using commercial gelatinous $Al(OH)_3$ e.g., Fischer Scientific Aluminum Hydroxide-Gelatinous, to prepare a HAP unit. The gelatinous $Al(OH)_3$ of this example equilibrates slowly to a pH of about 7.7.

EXAMPLE 3b

HAP Unit of $Al(OH)_3$ Gel

An alternative method of preparing the $Al(OH)_3$ gel is to dissolve anhydrous aluminum chloride in distilled $H_2O$ and titrated to an alkaline range, e.g., pH 9, with an NaOH solution, and stirred for 24 hours. After the 24 hour stirring step, the slurry is titrated with HCl until the desired pH (at which the liquid system is to be maintained, typically in the range of 7.1–8.0) is achieved. This transforms the material into a gelatinous suspension of $Al(OH)_3 \cdot nH_2O$. The gel is transferred to a dialysis tube as before and sterilized to complete the preparation of the HAP unit. For a unit titrated to pH 7.2, it still requires large amounts of additional acid to further decrease the pH to 6.8. This means the fresh gelationous aluminum hydroxide unit can be used to maintain the pH within a typically physiologic range.

The solid forms of aluminum (III) (i.e., anhydrous $Al(OH)_3$ and $Al_2O_3$ of Examples 1 and 2) equilibrate slowly, an approximate increase in solution pH of 0.1 units per day with aqueous medias to a final pH close to the physiological range (e.g., for $Al_2O_3$ the final pH is about 8.2). Thus, these materials can neutralize hydrogen ion at a rate similar to that at which many cellular systems produce it during storage.

Even though Al(III) is non-toxic to man below a concentration of 10 ppm, it does have an adverse effect on some biologicals (e.g., Aluminum (III) causes certain plasma proteins to aggregate). Thus, although a small amount of free $AL^{+3}$ can be tolerated, it is necessary to isolate the bulk of the aluminum from physical contact with the biologicals.

By placing the various gelatinous or solid forms of aluminum discussed above in Examples 1–3 in a sealed dialysis tube, isolation of the hydrogen ion acceptor (e.g., $Al(OH)_3$ gel) from the biologicals can be achieved while hydrogen ion is readily transported across the dialysis membrane. Such a combination allows for continuous removal of free hydrogen ion from high molecular weight or cellular systems without direct physical contact between the hydrogen ion acceptor and the biologicals.

The functional ability of the gelatinous system depends on two indispensible properties of the gelatinous aluminum hydroxide: namely, the ability of this material to absorb up to one-third its stoichiometric base equivalents without destroying its solid polymeric structure, and the effective high "molecular weight" of the polymer which prevents it from crossing the dialysis membrane.

pH CONTROL OF LIQUID SYSTEMS, EXAMPLES 4–14

EXAMPLE 4

Inorganic Salt Solution pH Control 1.0 g of each of aluminum hydroxide gel (prepared as in Example 3a above without sterilization), aluminum oxide powder (as in Example 2) were suspended in 100 ml aliquots of 0.85 wt % NaCl solution saturated with $CO_2$ to a pH of 5.7. Table 1 below shows the sorption of $H^+$ ions with consequent slow rise in pH to equilibrium over the time periods indicated. The samples were not enclosed in dialysis sacks.

TABLE I

| | pH of Sample | | |
|---|---|---|---|
| | | Sample | |
| Time | Saline Control | $Al(OH)_3$ gel | $Al_2O_3$ |
| 0 | 5.7 | 5.7 | 5.7 |
| 4 hrs | 5.7 | 7.6 | 8.2 |
| 1 day | 5.7 | 7.7 | 8.2 |
| 2 days | 5.7 | 7.7 | 8.0 |
| 3 days | 5.7 | 7.7 | 7.7 |
| 11 days | 5.7 | 7.4 | 7.3 |
| 12 days | 5.7 | 7.4 | 7.3 |
| 17 days | 5.7 | 7.3 | 7.2 |
| 25 days | 5.7 | 7.1 | 7.2 |

EXAMPLE 5

Neutralization of an Organic Weak Acid-Tetracycline

Duplicate sets of three samples of aluminum hydroxide gel (containing respectively 0.05 g, 1.0 g, and 5.0 g gel as in Examples 3a above) were sealed in cellophane dialysis sacks, each placed in 100 ml of 0.075% tetracycline HCl (a weak acid) in 0.85 wt % NaCl solution, and the pH measured over a 12 day period and compared to a duplicate pair of control tetracycline aliquots. The pH values are shown in Table II:

TABLE II

Mean pH Values

| | Sample | | | |
|---|---|---|---|---|
| Time | Control Tetracycline | .5g Al(OH)$_3$ gel | 1.0 g Al(OH)$_3$ gel | 5g Al(OH)$_3$ gel |
| 0 | 4.18 | 4.18 | 4.18 | 4.18 |
| 1 day | 4.26 | 6.55 | 6.88 | 7.26 |
| 6 days | 4.16 | 6.94 | 7.23 | 7.48 |
| 12 days | 4.25 | 7.16 | 7.38 | 7.55 |

The yellow colored tetracycline solution became clear and the gel in the HAP unit turned pink. At the end of the period, the control aliquots were titrated with 0.1 M NaOH solution to prepare a titration curve, and the base equivalents of the equilibrated aluminum hyroxide aliquots were determined from the curve. The base equivalents for each of the three weights of aluminum hydroxide were: for 0.5 g $=2.5\times10^{-2}$, for 1.0 g $=2.9\times10^{-2}$, and for 5.0 g $=3.1\times10^{-2}$ miliequivalents of NaOH. These results show that not only does aluminum hydroxide gel in a dialysis sack neutralize acid by passive acceptance, but it does not behave like a strong base, i.e., a 10-fold increase in acceptor material does not give rise to a 10-fold rise in base equivalents. Rather, the gel acts as if it were a weak base or buffering agent resulting in final pH values in the range 7.0 to 7.6. It is this behavior of aluminum hydroxide in a dialysis sack that permits its use in controlling pH in the physiological range.

EXAMPLE 6

MG(OH)$_2$-Enhanced HAP Units

The rate at which the aluminum-dialysis systems will neutralize hydrogen ion can be controlled in the HAP units by varying the type and amount of "inert" salts such as NaCl, KCl and MgCl$_2$ added. This is shown in more detail in Examples 7–14 below. However, the most pronounced changes occur when small amounts of other metal hydroxides are added to the aluminum. Table III below gives pH data (at 37° C.) for CPD stored blood control aliquots, aluminum hydroxide gel treated aliquots, and aluminum hydroxide with 1% by weight Mg(OH)$_2$ treated aliquots of human blood. From the Table III it can be seen that the addition of 1% Mg(OH)$_2$ to the aluminum hyroxide inside the dialysis sack allows for reduction of the required amount of aluminum hydroxide for pH control by ⅔, from 6 g per 100 ml whole blood to 2 g per 100 ml. Thus, in this invention the use of aluminum hydroxides and oxides to control pH includes not only the pure forms of these materials but also admixtures with various salts and metal hydroxides.

TABLE III pH Control with Mg-Enhanced Aluminum Hydroxide Gel

| | Sample | | |
|---|---|---|---|
| Days Stored at 4° C. | Control Standard CPD Blood | 6g Al(OH)$_3$ Gel | 2g Al(OH)$_3$ Gel 0.02 g Mg(OH)$_2$ |
| 0 | 7.175 | 7.175 | 7.175 |
| 7 | 7.040 | 7.165 | 7.190 |
| 14 | 6.940 | 7.170 | 7.180 |
| 20 | 6.835 | 7.075 | 7.120 |
| 28 | 6.785 | 7.035 | 7.045 |

EXAMPLES 7–14

Stored Blood pH Control

In these series of best mode examples, four-6 g samples of Al(OH)$_3$ gel mixture were prepared as in Example 3a, using 10 ml of a 0.85 wt % NaCl solution to suspend the 6 g of commercial Al(OH)$_3$ gel, and each sample of this preparation was loaded into a cellophane dialysis tube having a pore size of approximately 20A. The tube ends were sealed (by knotting) and the resulting HAP units were sterilized. Each of the four HAP units was placed in 100 ml aliquots of fresh whole human blood (having CPD anticoagulant) and are identified here as Examples 7a–10a. Identical 100 ml control blood aliquots, except for not employing HAP units, were also monitored by way of comparison and are identified as 7b–10b. The amount of the Al(OH)$_3$ gel system of the HAP units were predetermined by the volume of the blood to be treated to keep the whole blood pH between 7.0 and 7.2 when starting with an initial blood pH of 7.1. The amount of gel system for CPD or ACD blood ranges from 4–8 g gel in 10 ml 0.85 wt % saline per 100 ml ACD or CPD blood to be treated. This is true of whole blood or packed cells. Simple modification in the composition of the Al(OH)$_3$ matrix by changing salt concentration or adding strong bases capable of complexing to the Al matrix, can be used to shift the pH to higher or lower range within the limit 6.9 to 8.0.

FIGS. 3a–d graphically illustrate the results of pH measurements (at 37° C.) over the time period indicated (up to 28 days) for the CPD blood aliquots stored at 4° C. with HAP units (Examples 7a–10a), and prior art CPD blood aliquots stored at 4° C. without the units of this invention (Examples 7b–10b). In each case the HAP unit system of this invention maintains the blood at a pH above 7.0, while the normal, prior art CPD storage system and method results in the pH dropping to 6.8 or below.

Figure 4B:
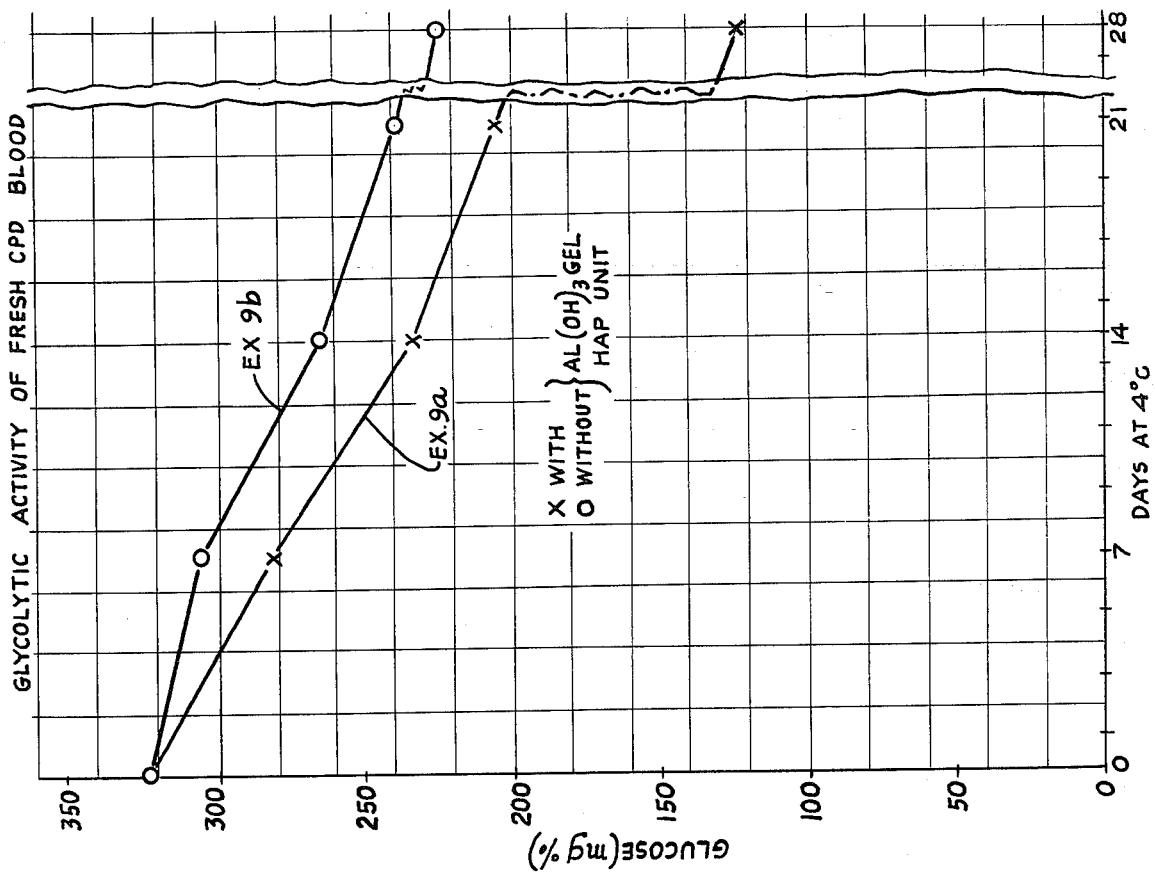
FIGS. 4a and 4b show typical examples of comparative glycolytic activity of stored blood both with and without the hydrogen acceptor system of this invention over a 28 day period.
Figure 4A:
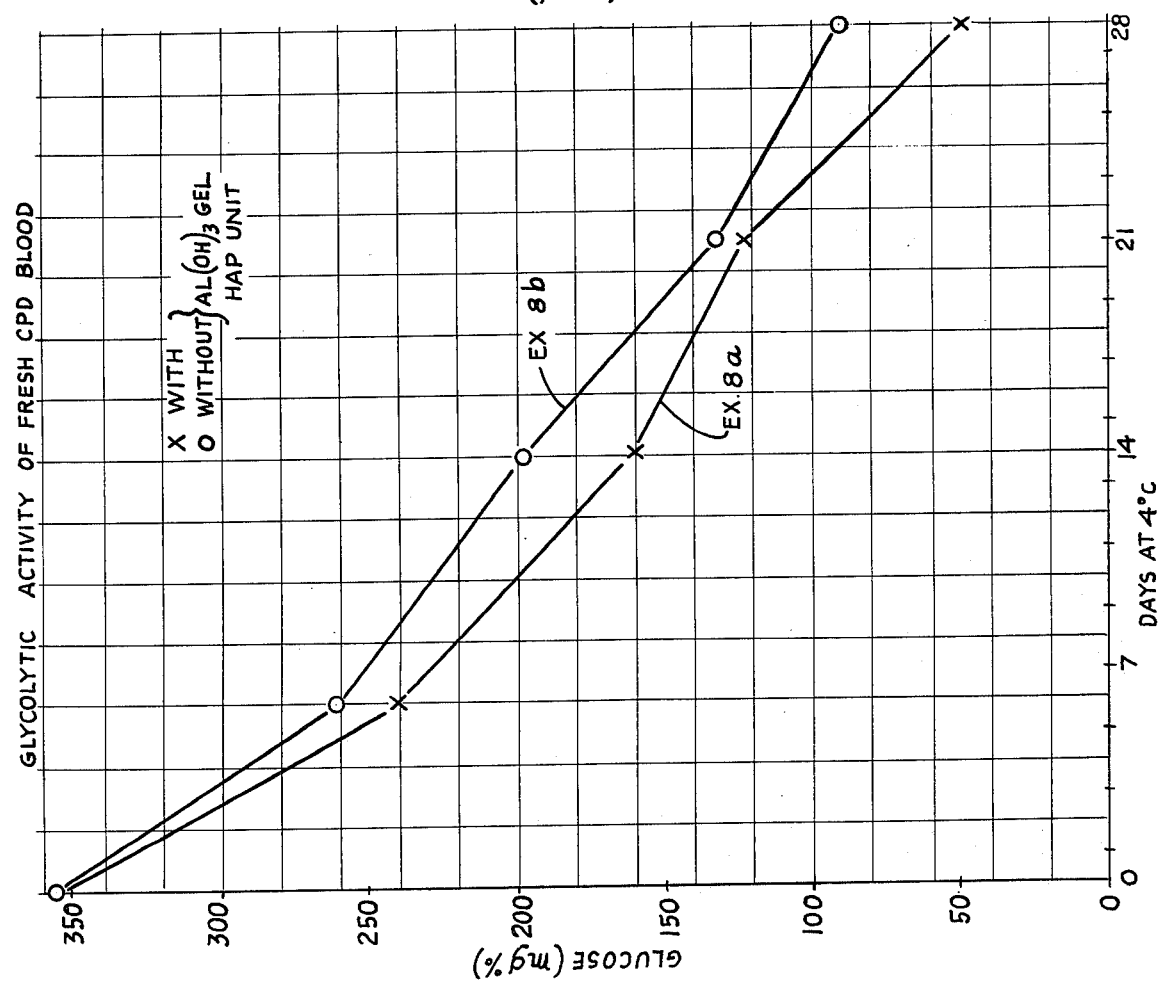

FIGS. 4a and 4b illustrate the unexpectedly improved results of the system and method of this invention, by enhancing or not inhibiting the red cell metabolism, by maintaining the glycolytic activity of fresh CPD blood. The two curves in FIG. 4a represent analysis of the mg% glucose in the blood of the sample aliquots of Examples 8a (with the HAP unit) and 8b (prior art CPD blood without the HAP unit), respectively. The upper curve of the prior art storage method shows that over the 28 day period the amount of glucose decreases as the red cells metabolize it. The lower curve of this invention shows an equal or slightly increased metabolism, demonstrating that the HAP units of this invention help support acceptable red cell metabolism during storage. FIG. 4b represents the metabolism of the Examples 9a and 9b aliquots, 9a, being the invention with the use of the HAP unit in CPD blood stored at 4° C. for 28 days, and curve 9b being the aliquot of Example 9b, prior art CPD blood without the HAP unit stored for the same period under the same conditions. Again, the comparative glucose levels of the two aliquots of the same fresh CPD blood illustrates equivalent or somewhat improved metabolism by use of the invention, and clearly no inhibition of RBC metabolism under storage conditions, thus demonstrating the HAP units are physiologically compatible.

Further, microscopic examination of red cell morphology showed no pathological problems associated with treatment of red cells by the HAP units or method of the invention. Measurement of plasma hemoglobin found the levels in aliquots treated in accord with the invention to be identical with those of the controls indicating that the invention does not induce red cell hemolysis. There were also no visual signs of plasma denaturation either in the bulk media or on the surfaces of the dialysis sacks in aliquots using the HAP units. These results indicate that not only does the invention maintain pH within the essential range of 7.0 to 7.2, but that it is also compatible with the complex biological system of whole human blood.

FIGS. 5a and 5b show the time history of ATP levels (measured in μmoles/100 ml) in comparative samples of stored CPD blood aliquots of Examples 8a and 8b (FIG. 5a) and Examples 9a and 9b (FIG. 5b). As noted above, the aliquots of Examples 8a and 9a are whole CPD blood stored for 28 days at 4° C. using the HAP units. The aliquots of the prior art methods are shown as curves labeled Examples 8b and 9b. It can be seen that the HAP unit treated aliquots of CPD whole blood have nearly identical ATP levels for the first 21 days, and thereafter the ATP levels are 20-30% higher than the prior art control aliquots. In addition, the control aliquot ATP level drops and stays below the normal in vivo ATP range, while the aliquots of this invention stay above or very close to the in vivo range.

Figure 6A:
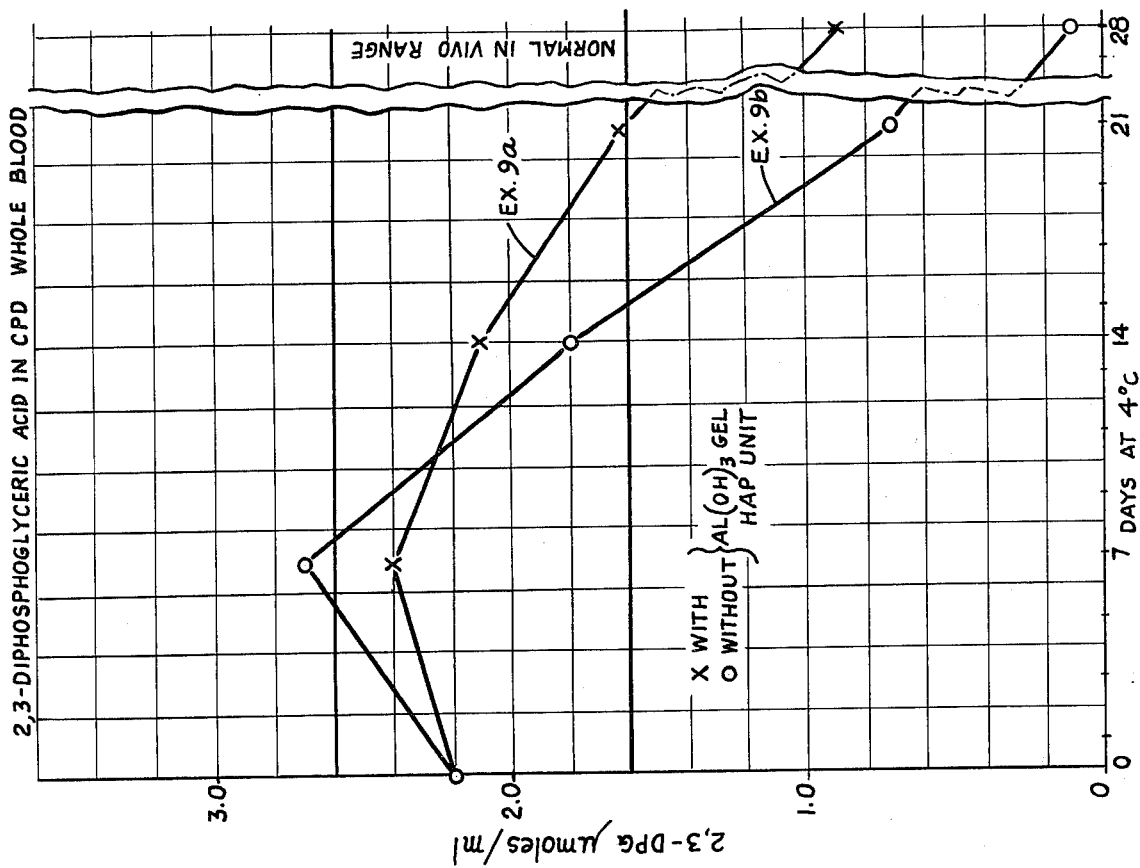
FIGS. 6a and 6b show typical improved results in the 2,3-DPG levels in stored whole blood in systems employing the present invention as compared to normal stored blood systems.
Figure 6B:
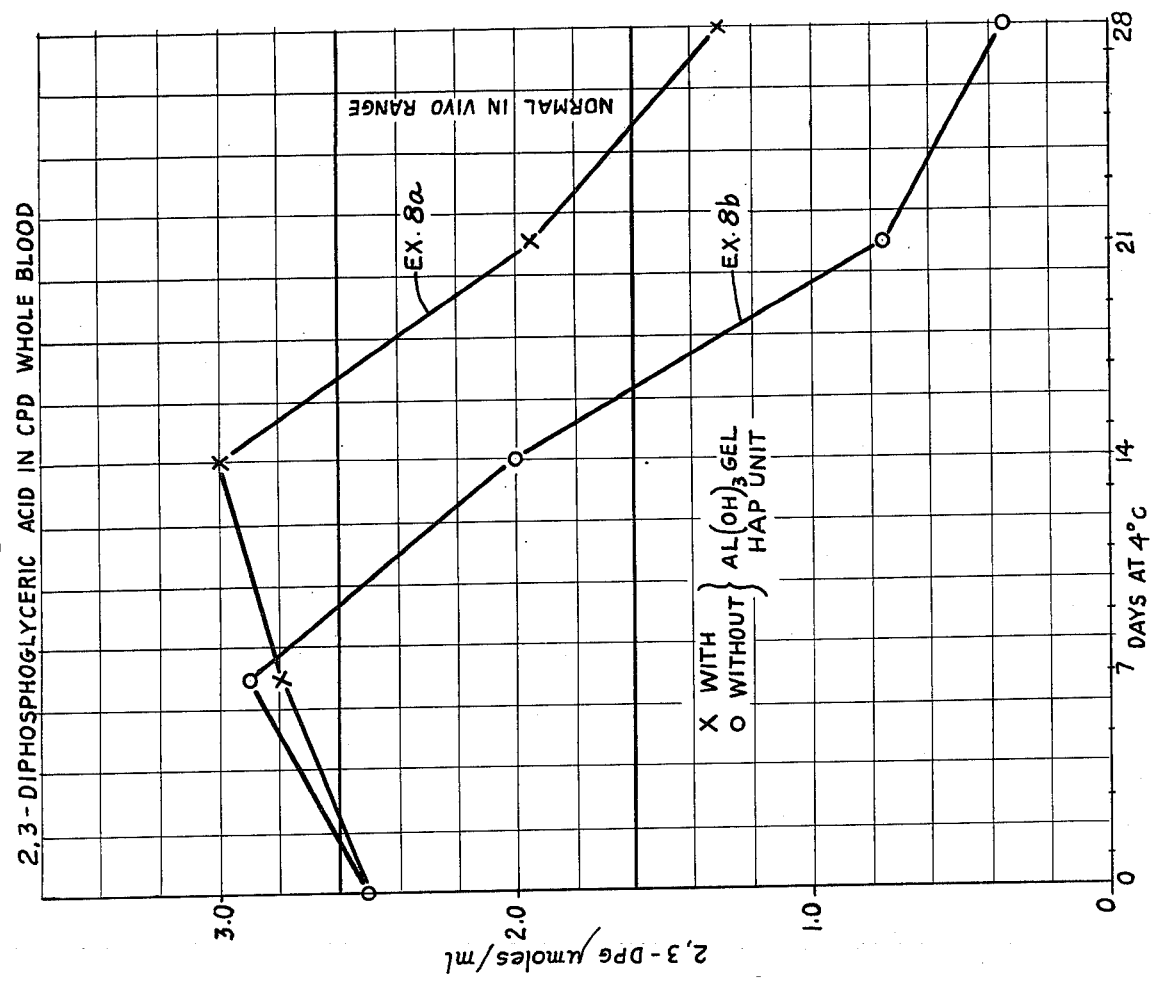

FIGS. 6a and 6b similarly show the 2,3-DPG levels in comparative aliquots of stored blood of Examples 8a and 9a (the invention) with Examples 8b and 9b (prior art CPD blood without HAP units). The 2,3-DPG levels of HAP unit treated blood is significantly higher than the standard of the prior art. At 3 weeks of storage, the treated aliquots (curves of Examples 8a and 9a) show from 75 to 100% more 2,3-DPG than the prior art controls.

Figure 7B:
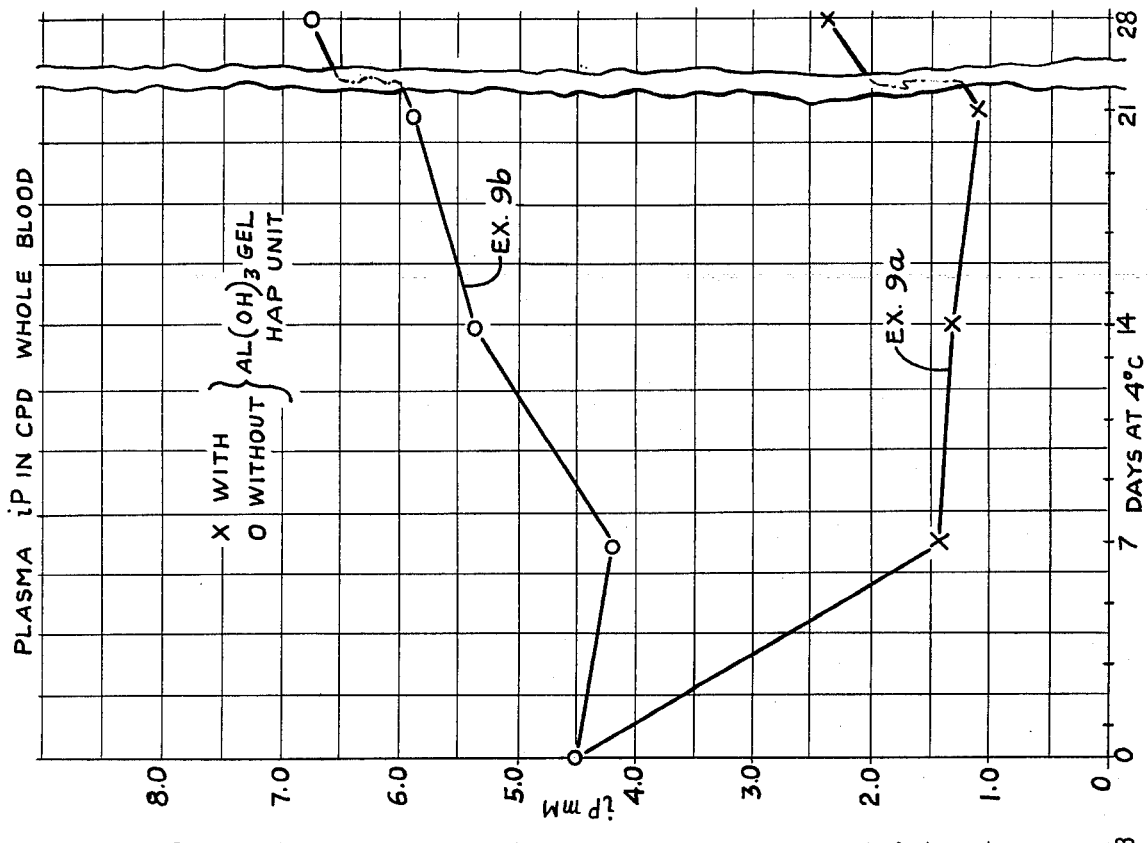
FIGS. 7a and 7b show improvement in maintenance of plasma inorganic phosphate in stored whole blood using the present invention as compared to the prior art methods and systems.
Figure 7A:
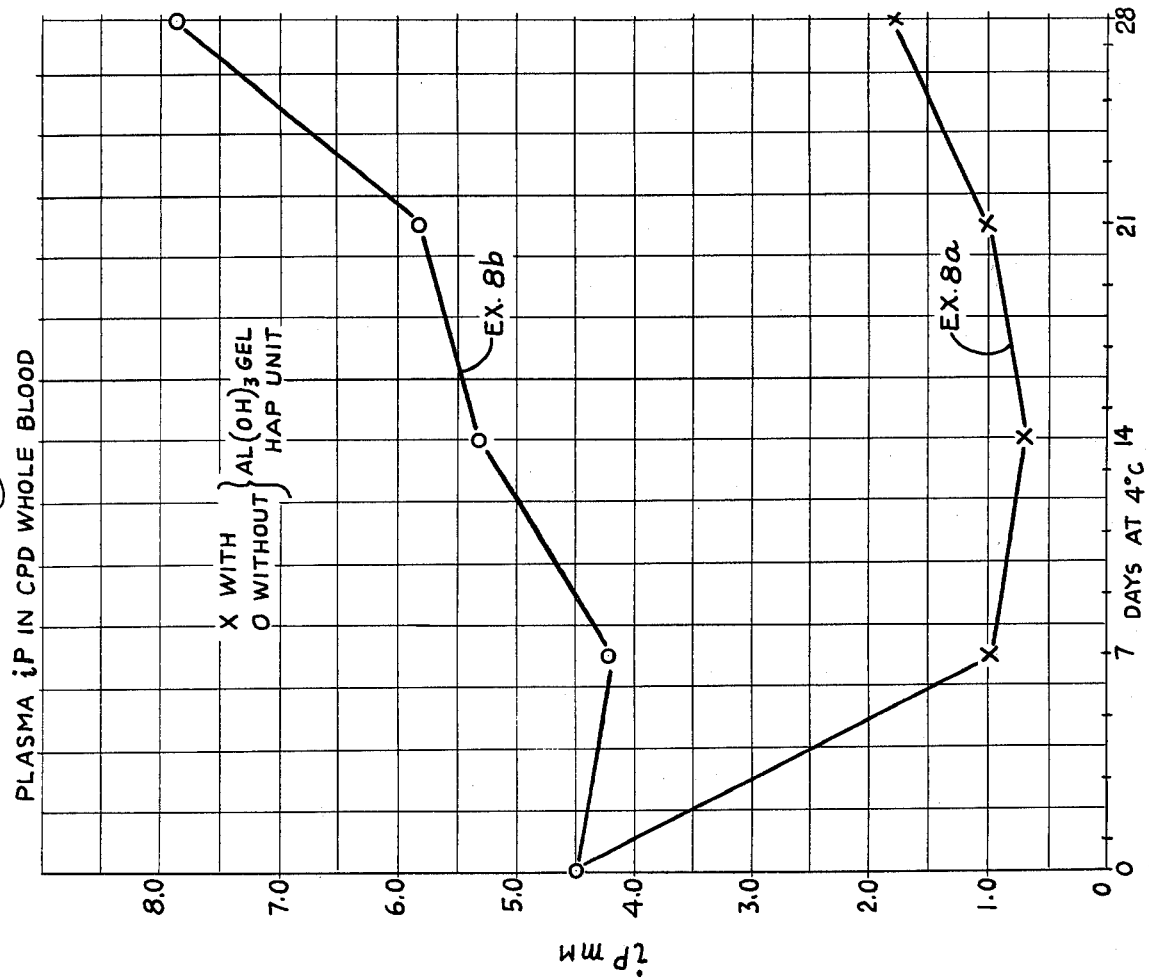

Substantial increases in plasma inorganic phosphate (iP) during latter periods of storage signify irreversible cell deterioration in ACD and CPD blood. FIGS. 7a and 7b show improved results using the HAP units of this invention, with FIG. 7a comparing Example 8a (using HAP unit) with its control Example 8b, and FIG. 7b showing Example 9a (using a HAP unit) with its control Example 9b. It is seen that the CPD controls Examples 8b and 9b utilize iP (i.e., plasma iP decreases) during the first week of storage where the pH remains above 7.0, but then the red cells lose iP (i.e., plasma iP increases) as they deteriorate, releasing organic phosphates to the plasma. However, this increase in plasma iP (signalling RBC deterioration) does not occur in the HAP unit treated aliquots. Thus, the continuous control of pH provided by the HAP unit aluminum-dialysis system prevents the irreversible damage of stored human red cells that occurs when they lose their ability to maintain their intracellular organic phosphates.

EXAMPLE 11 pH Control in ACD Blood

Three equal aliquots of 25 ml ACD human blood were evaluated, with the Example 11a aliquot employing a HAP unit as described above in Examples 7-10 having 1 g Al(OH)$_3$ gel, the Example 11b having an 2 g Al(OH)$_3$ gel HAP unit, and an Example 11c aliquot representing the prior art. The improved results during storage over a 20 day period are shown below in Table IV:

TABLE IV

| | Effect of HAP Units on ACD Blood (pH measurements) | | |
|---|---|---|---|
| | Examples | | |
| Time (days) | 11a 1g HAP Unit | 11b 2g HAP Unit | 11c Std. ACD Blood |
| 0 (draw day) | 6.95 | 6.95 | 6.95 |
| 1 | 7.01 | 7.07 | 6.92 |
| 2 | 7.03 | 7.14 | 6.88 |
| 3 | 6.97 | 7.19 | 6.83 |
| 5 | 6.95 | 7.23 | 6.79 |
| 8 | 6.95 | 7.25 | 6.73 |
| 15 | 6.87 | 7.08 | 6.54 |
| 20 | 6.81 | 7.00 | 6.47 |

It is concluded that 1 g is marginal while 2 g is more than sufficient, thus establishing a working range of from about 4-8 g of Al(OH)$_3$ gel/10 ml 0.85 wt % NaCl solution per 100 ml CPD or ACD blood, with 6 g being presently preferred as the best mode example. Other salts (besides NaCl) which may be employed in the aqueous ionic medium in which the acceptor material is carried or dispersed include KCl, MgCl$_2$ and mixtures thereof, alone or with NaCl.

EXAMPLE 12 Comparative Example Showing Ca(OH)$_2$ Hemolysis of Blood

Ca(OH)$_2$ either alone or in percentage greater than 5% by weight in the HAP unit is unacceptable for control of pH in the range 6.5 to 8.0. Further, such material results in the destruction of human red cells during storage at 4° C. rendering Ca(OH)$_2$ enclosed in dialysis tubing (see U.S. Pat. No. 3,953,329) unacceptable for control of blood pH under blood banking conditions.

In this example, two 100 ml aliquots of freshly drawn standard CPD blood were stored in contact with 6 grams of Al(OH)$_3$ gel alone in a sealed dialysis tube (Example 11a), 6 grams of Al(OH)$_3$ gel + 0.76 grams Ca(OH)$_2$ (Example 11b). The pH of each was measured over time as set forth in Table V below:

TABLE V

| | Blood Hemolysis with Ca(OH)$_2$ | |
|---|---|---|
| Day | Example 11a Al(OH)$_3$ gel unit pH | Example 11b Al(OH)$_3$ gel + 0.76 g Ca(OH)$_2$ pH |
| 0 | 7.22 | 7.22 |
| 1 | — | 8.13 |
| 2 | — | 8.59 |
| 3 | — | 8.94 |
| 4 | — | 9.09 |
| 7 | 7.16 | — |
| 14 | 7.11 | — |
| 21 | 7.03 | — |

By day 1 the red cells stored in the presence of the unit employing Ca(OH)$_2$ began to hemolyse while those stored in the presence of the unit employing only Al(OH)$_3$ gel showed no evidence of hemolysis. By day 7 all of the red cells stored in the presence of Ca(OH)$_2$ hemolysed while those stored in the presence of Al(OH)$_3$ gel only showed no evidence of red cell hemolysis even at 28 days of storage at 4° C.

EXAMPLE 13 Other Ion Acceptor Units

By way of a working example, ion acceptor materials and systems may be prepared using the oxides, hydroxides, phosphates and silicates of metals other than aluminum, e.g., Ti, B and Si, loaded into dialysis sacks and used to maintain the pH of aqueous liquid systems in the ranges described above, as either $H^+$ or $OH^-$ ion acceptors in HAP units, or hydroxide acceptor packets (OHAP units). Also as described above, $Al(OH)_3$ gel in the pH range above 8.0 functions to accept $OH^-$ ions.

EXAMPLE 14 $Mg^+$ Ion Enhancement

This example demonstrates a further implication of this invention, wherein use of $Mg^{+2}$ ion in the ion acceptor material system (within the packet) enhances the impact which pH control has on the physiological well being of red cells stored under blood banking conditions.

In this example freshly collected standard CPD blood was separated into three 100 ml aliquots; one aliquot served as control, another was stored with a HAP unit containing 6 grams $Al(OH)_3$ gel in the 0.85 wt % saline solution, and the third stored with a HAP unit containing 6 grams $Al(OH)_3$ gel in the 0.85 wt % saline solution mixed with 0.06 grams $MgCl_2$ as a source of $Mg^{+2}$. The pH of the three aliquots along with the remaining levels of ATP and 2,3-DPG in the whole blood aliquots are given in Table VI below:

TABLE VI

| | $Mg^+$ Ion Enhancement of Stored Whole Blood | | | | | | | | |
|---|---|---|---|---|---|---|---|---|---|
| | pH @ 37° C. | | | % Remaining of Initial ATP | | | % Remaining of Initial 2,3-DPG | | |
| Days Stored @ 4° C. | Control | Al (OH) gel Alone | Al (OH) gel + 1% MgCl | Control | Al (OH) gel Alone | Al (OH) gel + 1% MgCl | Control | Al (OH) gel Alone | Al (OH)$_3$ gel + 1% MgCl |
| 0 | 7.23 | 7.23 | 7.23 | 100% | 100% | 100% | 100% | 100% | 100% |
| 7 | 7.02 | 7.16 | 7.16 | 81% | 81% | 92% | 116% | 124% | 125% |
| 14 | 6.87 | 7.11 | 7.11 | 89% | 81% | 86% | 80% | 133% | 99% |
| 21 | 6.73 | 7.03 | 7.03 | 54% | 68% | 84% | 30% | 86% | 84% |
| 28 | 6.63 | 6.95 | 6.95 | 51% | 70% | 84% | 16% | 58% | 56% |

Under these conditions the $Mg^{+2}$ ion readily leaves the HAP unit and is available for utilization by the red blood cell resulting in significantly improved storage. It is important to note that this effect of $Mg^{+2}$ ion is not obtained when the pH is not maintained in the range 7.0-7.2. The $MgCl_2$ ranges from 0.01 to 2 wt % of the ion acceptor material.

An alternative system is to add $Mg^{+2}$ ion to the standard ACD or CPD anticoagulant solutions to be used in conjunction with pH control by a HAP unit not employing $MgCl_2$. The $Mg^{+2}$ ion concentration in the drawn blood in anticoagulant should be in the range of from about 0.01 to 5 millimolar. These solutions are as follows:

CPD-Mg Anticoagulant Solution 25.5 g trisodium citrate
3.2 g citric acid
2.18 g monobasic phosphate
25.0 g dextrose
2.3 g $MgCl_2$ (~24 millimolar)
diluted to 1000 ml with distilled water; 63 ml of this anticoagulant solution used with 450 ml of whole blood.

Similarly, 2.0 g (about 21.5 mM) of $MgCl_2$ is added to one liter of standard ACD to make the ACD Mg anticoagulant solution (about 75 ml volume is used for 450 ml whole blood preservation).

It is clear from the examples herein that: (1) control of pH in a complex biological system, typified by whole human blood during storage at 4° C., could be achieved using the HAP units of this invention (aluminum hydroxide gel sealed in a dialysis sack); (2) the method of pH control of this invention is compatible with both plasma and red cell components of the blood; (3) through pH control by the method of this invention, significant and unexpected improvements in red cell quality during storage at 3 to 4 weeks is obtained; (4) when red cell storage media pH is maintained between 7.0 and 7.2, the biochemical parameters considered important to red cell viability and function are maintained more closely to the levels found in vivo. The closer there is maintenance of these parameters to in vivo levels, the better the blood will be for transfusion and the more likely it can be stored longer. Accordingly, the present invention for continuous pH maintenance is an important breakthrough in the art of blood banking as well as in other biological areas. To my knowledge, in the literature to date there has been no improvements of the in vitro quality of red cells and CPD whole blood as significant as those reported here.

The invention shown and described is by way of example and it is to be understood that many changes and modifications may be made without departing from the spirit of the invention. The invention is not to be considered as limited to the embodiment shown and described except insofar as the claims may be so limited.

I claim:

1. An ion acceptor packet unit used for pH control of aqueous liquid systems containing ions selected from water soluble bases, water soluble acids, and mixtures thereof comprising in operative combination:
   (a) means for containing an ion acceptor material and for maintaining said ion acceptor material separated from said liquid system while permitting passage of said ions from said liquid system therethrough into contact with said ion acceptor material;
   (b) an inorganic, substantially water insoluble ion acceptor material disposed in said containing means;
   (c) said acceptor material having the property of bonding ions selected from the group comprising ions of water soluble acids and ions of water soluble bases;
   (d) said containing means:
      (i) being water permeable,
      (ii) permitting selective passage therethrough of said ions from said liquid system into contact with said acceptor material, and
      (iii) preventing passage therethrough of substantial amounts of said acceptor material into direct contact with said liquid system;
   (e) said acceptor packet unit passively removing ions from said liquid system at rates compatible with the rate of said ion occurrence in said liquid system.

2. A pH control unit as in claim 1 wherein said container means includes at least one surface having a selectively permeable membrane having micropores therein in the range of 5-25 Angstroms in size.

3. A pH control unit as in claim 2 wherein said membrane is selected from cellophane and polycarbonate film.

4. A pH control unit as in claim 2 wherein said container means comprises a dialysis tube selected from cellophane and polycarbonate film.

5. A pH control unit as in claim 1 wherein said acceptor material is a metal compound selected from a metal oxide, a metal hydroxide, a metal phosphate, a metal silicate and mixtures thereof.

6. A pH control unit as in claim 5 wherein said metal is selected from Ti, Al, B and mixtures thereof.

7. A pH control unit as in claim 1 wherein said acceptor material is doped with from 0.01 to 5% by weight of a compound selected from the oxides, hydroxides, and mixtures thereof of Mg, Ca, Zn, Fe, Cu, Co, Cr and V.

8. A pH control unit as in claims 5 or 7 wherein said acceptor material is doped with a cation selected from $Na^+$, and $K^+$ and mixtures thereof.

9. A pH control unit as in claim 6 wherein said metal is Al, and said acceptor material is selected from Al(OH)$_3$ gel, anhydrous Al(OH)$_3$, and Al$_2$O$_3$.

10. A pH control unit as in claim 9 wherein said acceptor material is doped with from 0.01 to 2 wt % of a strong base selected from the group Mg(OH)$_2$, ZnO, Zn(OH)$_2$, Fe$_2$O$_3$, Fe(OH)$_3$ and mixtures thereof.

11. A pH control unit as in claim 10 wherein said acceptomaterial is Al(OH)$_3$ gel and said dopant is Mg(OH)$_2$.

12. A pH control unit as in claims 1, 9, 10 or 11 wherein said acceptor material is dispersed in a water soluble salt solution.

13. A pH control unit as in claims 1, 9, 10 or 11 wherein said acceptor material is dispersed in an aqueous solution containing from about 0.03 g to 0.12 g NaCl/5 g acceptor material.

14. A pH control unit as in claims 1, 9, 10, or 11 wherein said acceptor material is dispersed in an aqueous solution containing from about 0.03 g to 0.12 g NaCl/5 g acceptor material, and from about 0.01 to 2.0 g MgCl$_2$/100 g acceptor material.

15. A method of controlling the pH of a liquid system having an initial pH in the range of from about 4.5 to 9.0 comprising the steps of:
(a) providing ion acceptor packet unit as in claim 1;
(b) contacting the exterior of said packet with liquid of said system for time sufficient to permit passage thereinto of sufficient ions to control the pH of the liquid system at a predetermined pH.

16. A pH control method as in claim 15 wherein said liquid system initial pH is in the range of from about 6.5 to 8.0.

17. A pH control method as in claim 16 wherein said liquid system is a blood substance and said initial pH is in the range of from about 6.9 to 7.5.

18. A method of controlling the pH of a blood substance during storage comprising the steps of:
(a) providing a hydrogen ion acceptor packet unit as in claim 9;
(b) disposing said packet in a blood storage bag;
(c) introducing a blood substance selected from the group consisting essentially of a blood component and whole ACD or CPD collected blood into said bag into contact with said packet; and
(d) maintaining said blood bag at 4° C. during storage.

19. Method of pH control of said blood as in claim 18 wherein said hydrogen ion acceptor material is Al(OH)$_3$ gel dispersed in an aqueous solution of from 0.03 to 0.12 g NaCl/5 g of acceptor material.

20. Method of pH control of said blood as in claim 19 wherein 4-8 g of said Al(OH)$_3$ gel is dispersed in 10 ml of 0.85 wt % NaCl solution per 100 ml of said ACD or CPD blood.

21. Method of pH control of said blood as in claim 19 wherein said Al(OH)$_3$ gel is doped with from 0.01 to 2% by weight of Mg(OH)$_2$.

22. Method of pH control of said blood as in claims 20 or 21 which includes 0.01 to 2 g MgCl$_2$ per 100 g of said acceptor material present in said hydrogen ion acceptor packet unit.

23. A pH control method as in claim 15 wherein said liquid system is an industrial fermentation process aqueous liquid.

24. In a method for continuously maintaining the pH of liquid stored mammalian blood subject to deterioration through cumulative metabolic acidosis, within a very narrow pH range of 7.0 to 7.2 for period of time ranging to at least 21 days, the steps of mixing said mammalian blood with an anticoagulant plasma medium and continuously maintaining the temperature of said blood plasma mixture within the range of 4° to 7° C., while maintaining contact of said blood mixture with a dialysis membrane in permeable communication with a hydrogen ion acceptor in the form of a dilute saline solution having dispersed therein a solid hydrogen ion acceptor material selected from the group comprising aluminum hydroxide gel, anhydrous aluminum hydroxide, aluminum oxide, and mixtures thereof, the rate of hydrogen ion acceptance of said acceptor medium being substantially equivalent to the rate of generation of hydrogen ions by said stored blood mixture.

25. A method as in claim 24 wherein said anticoagulant plasma medium is selected from CPD and ACD.

26. A method as in claim 25 wherein said anticoagulant plasma medium includes 0.01 to 5 millimoles $Mg^{+2}$ ions.

27. A method as in claim 24 wherein each 500 milliliter aliquot of said blood mixture is in fluid communication through said dialysis membrane with a dilute saline solution in the form of a 0.85% NaCl solution containing from about 25 to 40 grams of hydrogen ion acceptor material.

28. A method as in claim 27 wherein each said 500 milliliters of blood mixture comprises 450 milliliters of whole mammalian blood mixed with 63 milliliters of CPD solution.

29. A method as in claim 24 wherein said blood mixture is a red cell suspension in a CPD anticoagulant storage medium.

30. Liquid storage means for maintaining the pH of biological and biochemical liquid systems subject to deterioration through cumulative metabolic acidosis, within a very narrow pH range from 7.0 to 7.2, for periods of time not less than 21 days, comprising: a substantially biologically and biochemically inert enclosure for said liquid system, a dialysis sack disposed within said enclosure so as to be in contact with said liquid system, said dialysis sack containing a dilute salt solution which is biologically and biochemically inert as respects the components of said liquid system and a dispersed solid hydrogen ion acceptor material selected from the group comprising aluminum hydroxide gel, anhydrous aluminum hydroxide, aluminum oxide, and mixtures thereof.

31. Liquid storage means as in claim 30 wherein said liquid system is selected from the group comprising CPD and ACD anticoagulant formulations for blood preservation.

32. Liquid storage means as in claim 31 wherein said CPD and ACD formulations include 0.01 to 5 millimoles $Mg^{+2}$ ions.

33. Liquid storage means as in claim 30 wherein said substantially biologically and biochemically inert enclosure is a standard blood bag and said dialysis sack is an enclosed tubular section of biological grade cellulose membrane having a pore size of 20 A°.

34. Liquid storage means as in claim 30 wherein said dilute salt solution is a 0.85% by weight NaCl solution.

35. Liquid storage means as in claim 34 which includes from 0.01 to 2 weight % of $Mg(OH)_2$.

36. Liquid storage means as in claim 35 wherein said saline solution additionally includes from 0.01 to 2.0 g $MgCl_2$ per 100 g acceptor material.

37. Liquid storage means as in claim 30 wherein 4–8 g of said hydrogen ion acceptor material is dispersed in 10 ml of 0.85 weight % NaCl solution per 100 ml of said ACD or CPD blood.

38. Liquid storage means as in claims 30 or 37 wherein said saline solution additionally includes from 0.01 to 2.0 g $MgCl_2$ per 100 g acceptor material.

39. Liquid storage means as in claim 37 wherein said hydrogen ion acceptor material in $Al(OH)_3$ gel.

40. Method of producing an ion acceptor material packet for control of pH of liquid systems having initial pHs in the range of from 4.5 to 9.0 comprising the steps of:
 (a) selecting a matrixing ion acceptor material selected from an oxide, hydroxide, phosphate and silicate of a metal selected from Ti, Al and B,
 (b) mixing said ion acceptor material in an aqueous media having a source of anions capable of disrupting the lattice of said matrix,
 (c) introducing said material mixture into a container means including a dialysis membrane for passing selected ions from said liquid systems therethrough to be bound by said acceptor material, and
 (d) closing said container means to produce a sealed ion acceptor packet.

41. A method as in claim 40 which includes the step of sterilizing said closed ion acceptor packet.

42. A method as in claim 41 wherein said container means is a dialysis tube selected from cellophane and polycarbonate film.

43. A method as in claim 41 wherein said container means has a volume of from 14 to 18 ml/100 ml of said liquid system.

44. A method as in claim 43 wherein said matrixing material is selected from $Al(OH)_3$ gel, anhydrous $Al(OH)_3$, and $Al_2O_3$.

45. A method as in claim 44 wherein said aqueous mixing media is a salt solution containing from 0.03 g to 0.12 g salt/5 g acceptor material.

46. A method as in claim 45 wherein said salt solution is 0.85 wt % NaCl solution.

47. A method as in claims 45 or 46 which includes 0.01 to 2.0 g $MgCl_2/100$ g acceptor material in said salt solution.

48. A method as in claims 45 or 46 wherein said acceptor material is doped with from 0.01 to 2% by weight of a strong base selected from the group $Mg(OH)_2$, ZnO, $Zn(OH)_2$, $Fe_2O_3$, $Fe(OH)_3$, and mixtures thereof.

49. A method of controlling the pH of whole blood during storage comprising the steps of:
 (a) providing a hydrogen ion acceptor packet containing means having therein an acceptor material of a metal compound selected from a metal oxide, a metal hydroxide, a metal silicate and mixtures thereof, said metal being selected from Ti, Al, B and mixtures thereof
 (b) said acceptor material having the property of bonding ions selected from the group comprising ions of water soluble acids and ions of water soluble bases;
 (c) said containing means:
  (i) being water permeable,
  (ii) permitting selective passage therethrough of said ions from said liquid system into contact with said acceptor material, and
  (iii) preventing passage therethrough of substantial amounts of said acceptor material into direct contact with said liquid system;
 (d) said acceptor packet unit passively removing ions from said liquid system at rates compatible with the rate of said ion occurrence in said liquid system;
 (e) disposing said packet in a blood storage bag;
 (f) introducing whole ACD or CPD collected blood into said bag into contact with said packet;
 (g) drawing said collected blood into an anticoagulant solution selected from ACD and CPD solution with sufficient $MgCl_2$ to provide from 0.01 to 5 millimoles $Mg^{+2}$ ion in the resultant mixture of collected blood and anticoagulant; and
 (h) maintaining said blood bag at 4° C. during storage.

* * * * *